United States Patent
Chuang et al.

(10) Patent No.: US 9,223,747 B2
(45) Date of Patent: Dec. 29, 2015

(54) SYSTEM FOR REUSING TRIPLE EVENT DATA IN PET AND METHOD, PROGRAM PRODUCT THEREOF

(71) Applicant: National Tsing Hua University, Hsinchu (TW)

(72) Inventors: Keh-Shih Chuang, Hsinchu (TW); Hsin-Hon Lin, Hsinchu (TW)

(73) Assignee: National Tsing Hua University, Hsin-Chu (TW)

( * ) Notice: Subject to any disclaimer, the term of this patent is extended or adjusted under 35 U.S.C. 154(b) by 484 days.

(21) Appl. No.: 13/721,723

(22) Filed: Dec. 20, 2012

(65) Prior Publication Data
US 2014/0039831 A1  Feb. 6, 2014

(30) Foreign Application Priority Data
Jul. 31, 2012  (TW) .............................. 101127647 A (51) Int. Cl.
G06F 17/00 (2006.01)
A61B 6/03 (2006.01)
G01T 1/29 (2006.01)
A61B 6/00 (2006.01)

(52) U.S. Cl.
CPC ................ *G06F 17/00* (2013.01); *A61B 6/037* (2013.01); *A61B 6/4258* (2013.01); *A61B 6/5205* (2013.01); *G01T 1/2985* (2013.01)

(58) Field of Classification Search
CPC .... G01T 1/2985; A61B 6/037; A61B 6/4258; G06F 17/00
See application file for complete search history.

(56) References Cited

U.S. PATENT DOCUMENTS

2008/0111081 A1* 5/2008 Chuang .................... 250/363.03

OTHER PUBLICATIONS

Andreyev et al., Dual-Isotope PET Using Positron-Gamma Emitters, Jul. 21, 2011, Phys. Med. Biol. vol. 56, No. 14, pp. 4539-4556.*
Kacperski et al., Three-Gamma Annihilations as a New Modality in PET, 2004 IEEE, pp. 3752-3756.*
Andreyev et al. Abstract, Jul. 21, 2011, 3 pp.*

* cited by examiner

Primary Examiner — Toan Le
(74) Attorney, Agent, or Firm — WPAT. P.C.; Anthony King (57) ABSTRACT

The invention provides a system for reusing triple event data of PET. The system includes an input unit, a determining unit, and an output unit. A plurality of data is generated by an object undergoing the PET scan, and the input unit is used to receive the data. The determining unit is used to determine the data and pick out data corresponding to triple event from the data and according to a formula to pick out data corresponding to coincident event from the data corresponding to triple event. In other words, the determining unit picks out data corresponding to true triple event from the data to reuse and analyze the data corresponding to coincident event and further to generate an analysis result. The output unit is used to output the analysis result.

24 Claims, 6 Drawing Sheets

SYSTEM FOR REUSING TRIPLE EVENT DATA IN PET AND METHOD, PROGRAM PRODUCT THEREOF

CROSS-REFERENCE TO RELATED APPLICATIONS

This Non-provisional application claims priority under 35 U.S.C. §119(a) on Patent Application No(s). 101127647 filed in Taiwan, Republic of China 07, 31, 2012, the entire contents of which are hereby incorporated by reference.

FIELD OF THE INVENTION

The invention is a system, method, program product for reusing data, especially relatively to the system, method, program product for reusing triple event data of PET.

BACKGROUND OF THE INVENTION

Positron emission tomography (PET) is a technology of functional medical image detection. PET is based on the theory (Annihilation Coincident Detection, ACD) that a positron and an electron annihilate with each other to generate a pair of annihilation photons.

Figure 1:
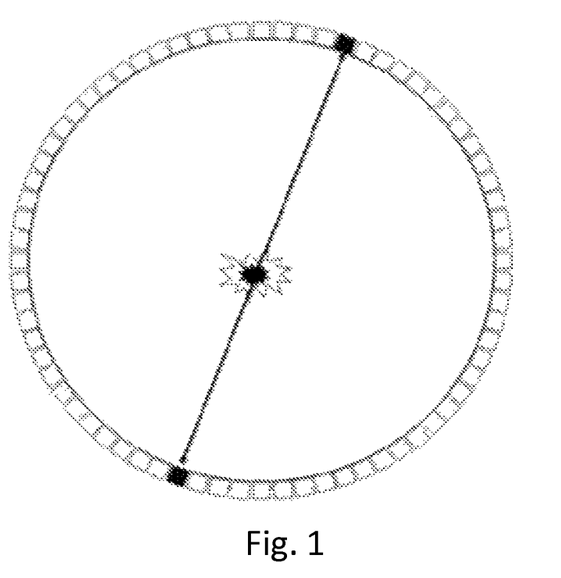
FIG. 1 is a diagram showing the pair of annihilation photons.

FIG. 1 is a diagram showing the pair of annihilation photons. The pair of annihilation photons with 511 keV energy have high probability to pass through an object. When the pair of photons are detected by detector pair of a detector around the object in a short time interval, it means a coincident event.

The short time interval is also called coincidence timing window or time window. The route of two photons being detected is called line of response (LOR). All coincident events occurred on LOR are listed in the counts of the detector. Finally, stacking all the LORs with different angles and different positions can get a Sinogram, and further to calculate and reconstruct all of the data to form a PET image.

During PET scanning, if more than three photons are detected in the same time window defined by a system, it's called multiple event which also comprises triple event. The information of multiple event doesn't be taken record because it is can not be determined that which position detected are the pair of annihilation photons occurring at, even can not be determined which photons are annihilation photons.

Therefore, in convention, almost data of triple event are abandoned to avoid erroneous determination. Besides, when the object includes higher activity, the probability of triple event becomes higher, the more data are abandoned. These data can not provide any useful help in the technology after being abandoned and it wastes much useful information.

SUMMARY OF THE INVENTION

The invention provides a system for reusing triple event data of PET. The system of the invention can determine which two photons are a pair of annihilation photons and further to reuse the data. The system for reusing triple event data of PET comprises an input unit, a determining unit, and an output unit.

A plurality of data is generated by an object undergoing the PET scan, and the input unit is used to receive the data. The determining unit is used to determine the data and pick out data corresponding to triple event from the data and according to a formula to pick out data corresponding to coincident event from the data corresponding to triple event. In other words, the determining unit picks out the data corresponding to true triple event from the data to reuse and analyze the data corresponding to coincident event and further to generate an analysis result. The output unit is connected with the determining unit to output the analysis result.

A plurality of data is generated by an object undergoing the PET scan, and the data comprises different events with single photon, double photons, and triple photons detected. The invention drops out the data of single photon, and uses data of double photons, and further picks out the data corresponding to coincident event from the data corresponding to triple event according to a formula. According to the probability ($P_t$) of arriving time, the probability ($P_L$) of side length, the probability ($P_S$) of Sinogram, the object probability ($P_O$), the energy probability ($P_E$), the formula can find out the probability and indicate the LOR with largest probability as the true event of triple event, and further reuse the data.

The invention also provides a method for reusing triple event data of PET, and the steps are as follows:

Step. 1 A plurality of data is generated by an object undergoing the PET scan, and the data comprises data corresponding to triple event.

Step. 2 Said data corresponding to triple event are picked out from the data. According to a formula, data corresponding to coincident event are picked out from the data corresponding to triple event.

Step. 3 The data corresponding to coincident event is reused and analyzed to generate an analysis result.

The method for reusing triple event data of PET can be applied to a program product. The program product of PET has a non-transient readable medium and is installed in a processor. When the processor executes the program product, the data of triple event corresponding to coincident event is reused to output an analysis result. Furthermore, when PET installed the program product executes, the processor can simultaneously executes the method of reusing the data of triple event corresponding to coincident while the positron emission tomography is scanning. It can efficiently decrease the scanning time.

The system and the method of invention can reuse and analyze the data of triple event corresponding to coincident event to increase the counting number of the system and further to improve the sensitivity of PET system. It also can efficiently decrease the scanning time and decrease the use of radiation activity, and further to decrease patient's total radiation dose.

These and other features, aspects and advantages of the disclosure will become better understood with regard to the following description, appended claims, and accompanying drawings.

DETAILED DESCRIPTION OF THE INVENTION

For clarity of disclosure, and not by way of limitation, the detailed description of the invention is divided into the subsections that follow.

Figure 2A:
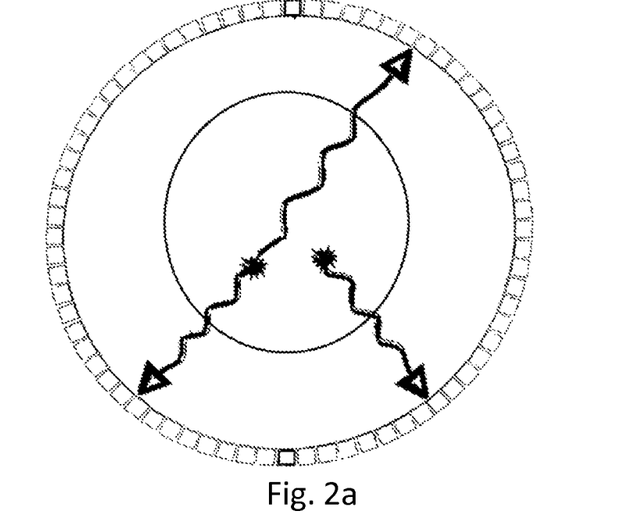
FIG. 2a is a diagram showing true triple event.
Figure 2B:
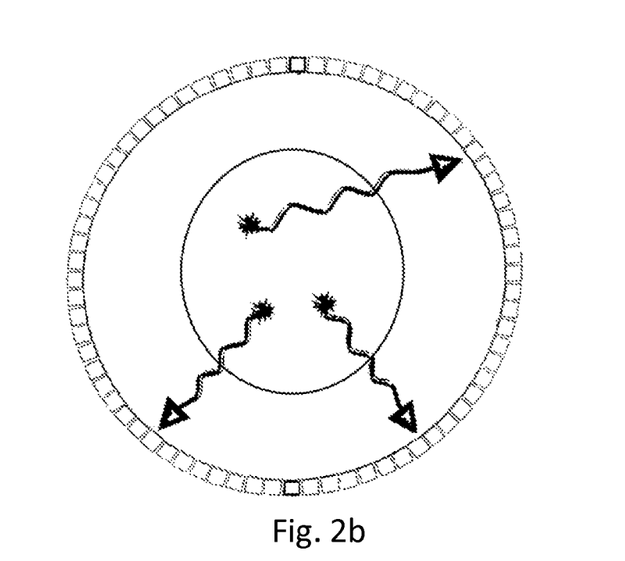
FIG. 2b is a diagram showing random triple event.

During PET scanning, if three photons are detected in a same time window defined by a system, it's called triple event. Moreover, if the triple event is formed by a pair of annihilation photons and another photon, it's called true triple event. FIG. 2a is a diagram showing true triple event, true triple event often occurs. If the triple event is formed by three photons occurring at different annihilation positions, it's called random triple event. FIG. 2b is a diagram showing random triple event, random triple event less occurs. In true triple event, if the pair of annihilation photons can be found, the data of the pair of annihilation photons can be reused.

Figure 3:
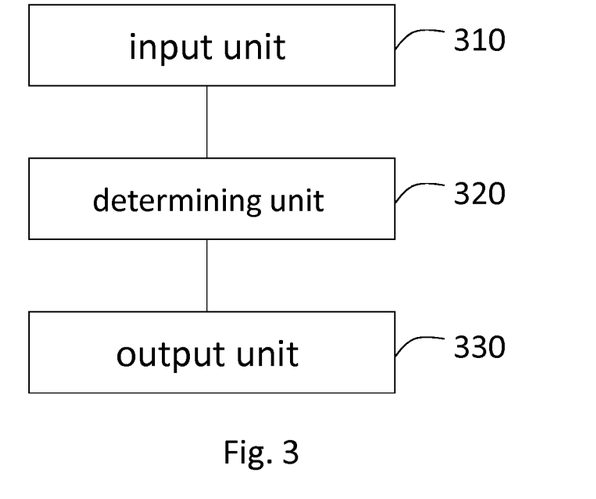
FIG. 3 is a diagram showing the system for reusing triple event data of PET in the invention.

The invention provides a system for reusing triple event data of PET. The system of the invention can determine which two photons are the pair of annihilation photons and further to reuse the data. FIG. 3 is a diagram showing the system for reusing triple event data of PET. The system for reusing triple event data of PET comprises an input unit 310, a determining unit 320, and an output unit 330.

A plurality of data is generated by an object undergoing the PET scan, and the input unit 310 is used to receive the data. The determining unit 320 is used to determine the data and pick out data corresponding to triple event from the data and according to a formula to pick out data corresponding to coincident event from the data corresponding to triple event. In other words, the determining unit 320 picks out data corresponding to true triple event to reuse and analyze the data corresponding to coincident event and further to generate an analysis result. The output unit 330 is connected with the determining unit 320 to output the analysis result.

In an embodiment, a positron emitter of PET is non-pure positron emitter, such as $^{22}$Na、$^{124}$I、$^{76}$Br、$^{86}$Y in the invention. The positron emitter of PET can also be pure positron emitter, such as $^{11}$C、$^{13}$N、$^{15}$O、$^{18}$F, but not limited herein.

Figure 4:
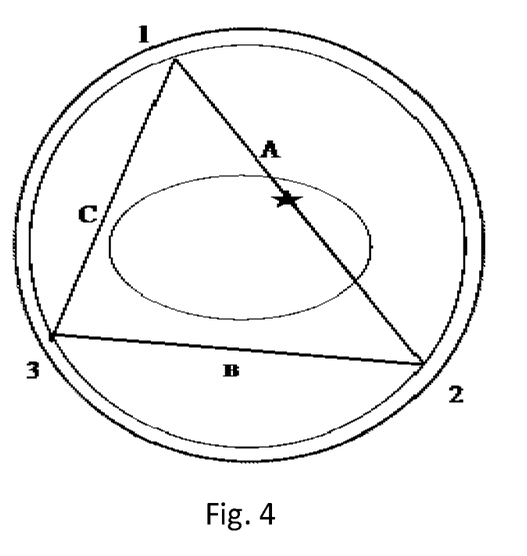
FIG. 4 is a diagram showing triple event.

FIG. 4 is a diagram showing triple event. In triple event, three photons are detected at different positions 1, 2, 3 of detector. The positions 1, 2, 3 are used to form a triangle, and the lengths of three sides are respectively three lines of response (LOR) A, B, C. One of the LOR A, B, C may be the LOR of true event. The following are the basic theories of the invention:

(1) The probability ($P_t$) of arriving time is defined as $P_t = \exp-(\Delta t/T)$. $\Delta t$ is the time difference of two photons of LOR arriving the detector, and T is the time resolution of the system. Theoretically the two annihilation photons occur and arrive the detector at the same time. However, in fact, since the time resolution of the system may be not accurate enough or the time difference of the two photons moving, the time that the two photons respectively arrive the detector may be little different. The time that the third photon arrives the detector is usually not the same as that of the pair of annihilation photons. As a result, the smaller time difference of the LOR is the greater probability of true event.

(2) The probability ($P_L$) of side length is defined as $$P_L = \frac{x^2}{a^2 + b^2 + c^2},$$

wherein, a, b, c are respectively the lengths of LOR A, B, C, $x \in (a, b, c)$. Since the two annihilation photons move in opposite direction along a line, the greater side length of the LOR in the triangle are more likely to be true event.

(3) The probability ($P_S$) of Sinogram is defined as $$P_S = \frac{S(x)}{S(A) + S(B) + S(C)},$$

wherein S(x), S(A), S(B), S(C) respectively mean the value on the Sinogram, $x \in (A, B, C)$. The value on the Sinogram means the total activity of the LOR through the object. As a result, the greater value the greater probability of the LOR is true event.

(4) The object probability ($P_O$) means that if LOR passes through the object, $P_O$ is defined as the value of 1. If LOR doesn't pass through the object, $P_O$ is defined as the value of 0 in the invention, because LOR is sure to pass through the object in true event.

(5) The energy probability ($P_E$) is defined as $P_E = \min(1, \exp[(E_X-511)/\Delta E]) \times \min(1, \exp[(E_Y-511)/\Delta E])$, as wherein, $E_X$ and $E_Y$ respectively mean the energy of the two photons of LOR, and $\Delta E$ means the energy window. The energy of the two annihilation photons is 511 keV. In normal situation, after scattering, the energy of photons is less than 511 keV. As a result, the photons which energy closer to 511 keV is more likely to be annihilation photons.

In an embodiment, according to three parameters of time difference of three photons arriving a detector, three lengths of LOR, total activity of the three LOR through the object in triple event, the formula of the invention respectively calculates and transforms the three parameters into three first probability values ($P_1$).

The formula comprises the step that determining if the largest first probability value ($P_1$) is greater than twice of the sum of the other two first probability values ($P_1$) [$P_{1(A)} > 2(P_{1(B)} + P_{1(C)})$], if yes, the determining unit 320 reuses the data corresponding to the largest first probability value ($P_1$), if not, the determining unit 320 drops out the data, but not limited herein.

Moreover, the each first probability value ($P_1$) is the product of the time probability ($P_t$) of a photon arriving the detector, the length probability ($P_L$) of LOR and total activity probability ($P_S$) of the LOR through the object. That is to say the product of $P_1 = P_t \cdot P_L \cdot P_S$, but not limited herein.

In another embodiment, according to three parameters of the first probability values ($P_1$), the situation if the photon through the object ($P_O$) and the photon energy ($P_E$) in triple event, the formula of the invention respectively calculates and transforms the three parameters into three second probability values ($P_2$).

The formula comprises the step that determining if the largest second probability value ($P_2$) is greater than twice of the sum of the other two second probability values ($P_2$), if yes, the determining unit 320 reuses the data corresponding to the largest second probability value ($P_2$), if not, the determining unit 320 drops out the data.

Furthermore, the each second probability value ($P_2$) is the product of the first probability value ($P_1$), the probability of the photon through the object ($P_O$) and photon energy probability ($P_E$). That is to say the product of $P_2 = P_t \cdot P_L \cdot P_S \cdot P_O \cdot P_E$, but not limited herein.

The product of $P_1 = P_t \cdot P_L \cdot P_S$ and the product of $P_2 = P_t \cdot P_L \cdot P_S \cdot P_O \cdot P_E$ are respectively defined as the probability of the LOR being true event in the invention. Moreover, the invention can increase accuracy through the formula to pick out the data with high probability. When calculating each probability of LOR of triple event, the largest probability value of LOR is used to compare with the sum of the other two probability values of LOR, if yes, the LOR with largest probability is indicated true event, and the data can be reused, but not limited herein.

In an embodiment, the formula is according to a relation between LOR and field of view (FOV) to picks out the data corresponding to coincident event from the data corresponding to triple event. For example, first, determines if the LOR is in the range of FOV according to the formula. When only one LOR is in the range of FOV, it is defined that the LOR is formed by the pair of annihilation photons, and when two LORs are both in the range of FOV, it is defined that the LOR with larger length is formed by the pair of annihilation photons, but not limited herein.

In an embodiment, the formula is according to a relation between LOR, FOV and photon energy to picks out the data corresponding to coincident event from the data corresponding to triple event. For example, first, finds all LORs of the three photons detected in triple event according to the formula. Then determines that the photon at opposite to the shortest LOR is one of the pair of annihilation photons according to the formula. After making sure the photon is one annihilation photon, then determines if the two LORs of the annihilation photon with other two photons is in the range of FOV according to the formula. When only one LOR is in the range of FOV, it is defined that the LOR is formed by the pair of annihilation photons, and when two LORs are both in the range of FOV, it is defined that the photon with lower energy is the other annihilation photon, and further to find out the pair of annihilation photons, but not limited herein.

In an embodiment, the formula is according to a relation between the energy of the three photons and an energy threshold to picks out the data corresponding to coincident event from the data corresponding to triple event. For example, when the energy of the one of the three photons detected is larger than the energy threshold, and the energy of the other two photons is less than the energy threshold, the other two photons are determined to the pair of annihilation photons, but not limited herein.

In an embodiment, when the energy of the three photons detected are all less than the energy threshold, the formula is according to a relation between LOR and FOV to picks out the data corresponding to coincident event from the data corresponding to triple event.

In an embodiment, when the energy of the three photons detected are all less than the energy threshold, the formula is according to a relation between LOR, FOV and energy of the three photons to picks out the data corresponding to coincident event from the data corresponding to triple event.

It's known from above that according to LOR, FOV, energy of photons, the formula of the invention can picks out the data corresponding to coincident event from different kinds of triple event, but not limited herein.

Figure 5:
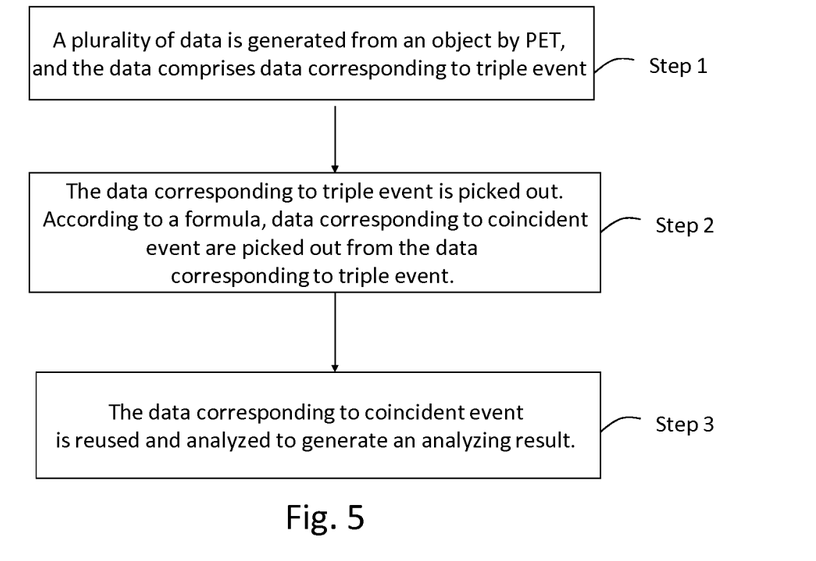
FIG. 5 is a flowchart showing the method for reusing triple event data of PET in the invention.

The invention also provides a method for reusing triple event data of PET, FIG. 5 is a flowchart showing the method for reusing triple event data of PET, and the steps are as follows:

Step. 1 A plurality of data is generated by an object undergoing the PET scan, and the data comprises data corresponding to triple event.

Step. 2 The data corresponding to triple event is picked out. According to a formula, data corresponding to coincident event are picked out from the data corresponding to triple event.

Step. 3 The data corresponding to coincident event is reused and analyzed to generate an analysis result.

Figure 6:
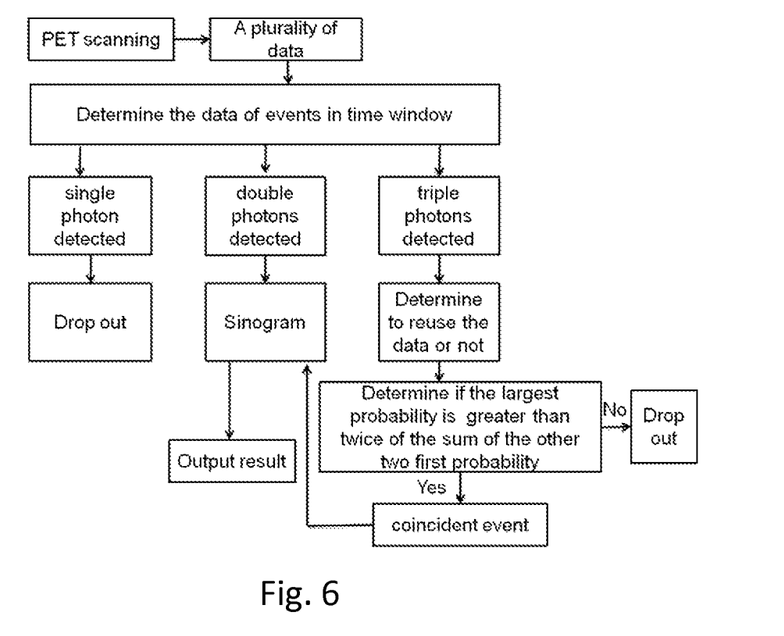
FIG. 6 is an organization chart showing the method for reusing triple event data of PET in the invention.

FIG. 6 is an organization chart showing the method for reusing triple event data of PET. A plurality of data is generated by an object undergoing the PET scan, and the data comprises different events with single photon, double photons, and triple photons detected. The invention drops out the data of single photon, and uses data of double photons, and further picks out the data corresponding to coincident event from the data corresponding to triple event according to a formula. According to the probability ($P_t$) of arriving time, the probability ($P_L$) of side length, the probability ($P_S$) of Sinogram, the object probability ($P_O$), the energy probability ($P_E$), the formula can find out the probability, and indicate the LOR with largest probability as the true event of triple event, and further to reuse the data.

The method for reusing triple event data of PET can be applied to a program product. The program product of PET has a non-transient readable medium and is installed in a processor. When the processor executes the program product, the data of triple event corresponding to coincident event is reused to output an analysis result with high sensitivity. Furthermore, when PET installed the program product executes, the processor can simultaneously executes the method of reusing the data of triple event corresponding to coincident while an object is undergoing the PET scan. It can efficiently decrease the scanning time.

Please refer to table 1 and table 2 respectively showing the information of normal PET and animal PET to detecting a phantom by using the method for reusing triple event data of the invention.

The table 1 shows the information of the normal PET detecting a phantom of various activities (x,y,z mCi) (The improvement of NECR increase when higher activity was used. I will suggest to include the activity in both Table 1 and 2. Change 1, 2, and 3 into actual activity used) by using the method for reusing triple event data of the invention.

TABLE 1

| | Double coincidence (original data) | | | | Triple | | Recycled | | | reusing rate |
|---|---|---|---|---|---|---|---|---|---|---|
| | True | Scatter | Random | NECR* | Total | True (reusable) | True (reused) | S + R | NECR | |
| 1 | 771,976 (41.8%) | 505,627 | 568,378 | 246,834 | 210,864 | 102,986 (49%) | 102,269 (74.5%) | 34,947 | 297,870 | 99.3% |
| 2 | 1,678,724 (57.3%) | 490,254 | 758,241 | 764,657 | 404,968 | 264,134 (65%) | 261,068 (81%) | 61,667 | 932,012 | 98.8% |
| 3 | 1,370,269 (53.3%) | 506,123 | 692,766 | 575,623 | 343,812 | 208,409 (61%) | 204,909 (75%) | 66,388 | 696,295 | 98.3% |

The table 2 shows the information of the animal PET detecting a phantom of various activities (x,y,z mCi) by using the method for reusing triple event data of the invention.

TABLE 2

| | Double coincidence (original data) | | | | Triple | | Recycled | | | reusing rate |
|---|---|---|---|---|---|---|---|---|---|---|
| | True | Scatter | Random | NECR* | Total | True (reusable) | True (reused) | S + R | NECR | |
| 1 | 2,165,166 (39.1%) | 672,555 | 2,693,957 | 569,919 | 1,282,223 | 649,262 (51%) | 619,016 (74.%) | 221,284 | 843,821 | 95.3% |
| 2 | 2,658,051 (45.4%) | 401,414 | 2,797,860 | 816,307 | 1,418,168 | 825,312 (58%) | 743,959 (76%) | 230,101 | 1,182,588 | 90.1% |
| 3 | 2,183,254 (39.4%) | 664,481 | 2,692,787 | 578,941 | 1,290,944 | 656,857 (51%) | 616,855 (73%) | 230,595 | 851,434 | 93.9% |

It's shown from the table 1 and the table 2 that the proportion of triple events and true events is approximately 25%-30% (even up to 50%). It also means the occurring probability of true events is high. Reusing rate of detecting three kinds of phantoms equals to the number of reused triple event/the number of reusable true event. The reusing rate is improved up to 90% by the method of the invention reusing triple event data of PET. The noise equivalent count rate (NECR) is improved 20%, even improved 48% on animal PET. As a result, the system and the method of the invention reusing triple event data of PET indeed have high efficiency.

$$\left(NECR = \frac{T^2}{T+S+2R}\right)$$

The system and the method of invention can reuse and analyze the data of triple event corresponding to coincident event to increase the counting number of the system and further to improve the sensitivity of PET system. It also can efficiently decrease the scanning time and decrease the use of radiation activity, and further to decrease patient's total radiation dose.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. A system for reusing triple event data of positron emission tomography, the system comprising:
   a positron emission tomography scan device;
   an input unit, used to receive a plurality of data generated from the positron emission tomography scan device, wherein the data comprising different events with photons detected;
   a determining unit, connected with the input unit, dropping out the data corresponding to single event, picking out the data corresponding to double event, then picking out the data corresponding to triple event from the data, and calculating three parameters of time difference of three photons detected by the positron emission tomography scan device, three lengths of line of response (LOR) and total activity of the three LOR through the object in triple event to obtain three first probability values by a formula, determining whether one of the largest first probability value is greater than twice of the sum of the other two first probability values, if yes, picking out the data with the largest first probability value, if not, dropping out the data, and analyzing the data which have not been dropped out to generate an analysis result; and
   an output unit, connected with the determining unit to output the analysis result.

2. The system according to claim 1, wherein the each first probability value is the product of the time probability of a photon arriving the detector, the length probability of LOR and total activity probability of the LOR through the object.

3. The system according to claim 1, wherein the determining unit further comprising:
   calculating the first probability values, the situation if the photon through the object and the photon energy in triple event, to obtain three second probability values, and determining whether one of the largest second probability value is greater than twice of the sum of the other two second probability values, if yes, picking out the data with the largest second probability value, if not, dropping out the data.

4. The system according to claim 3, wherein the each second probability value is the product of the first probability value, the probability of the photon through the object and photon energy probability.

5. The system according to claim 1, wherein a positron emitter of the positron emission tomography is non-pure positron emitter or pure positron emitter.

6. The system according to claim 5, wherein the non-pure positron emitter comprises $^{22}$Na、$^{124}$I、$^{76}$Br、$^{86}$Y.

7. The system according to claim 5, wherein the pure positron emitter comprises $^{11}$C、$^{13}$N、$^{15}$O、$^{18}$F.

8. The system according to claim 1, wherein the formula is according to a relation between LOR and field of view (FOV) to picks out the data corresponding to coincident event from the data corresponding to triple event.

9. The system according to claim 8, wherein the formula is according to a relation between LOR, FOV and photon energy to picks out the data corresponding to coincident event from the data corresponding to triple event.

10. The system according to claim 1, when the energy of the one of the three photons detected is larger than the energy threshold, and the energy of the other two photons are both less than the energy threshold, the other two photons are determined to a pair of annihilation photons.

11. The system according to claim 10, when the energy of the three photons detected are all less than the energy threshold, the formula is according to a relation between LOR and FOV to picks out the data corresponding to coincident event from the data corresponding to triple event.

12. The system according to claim 11, when the energy of the three photons detected are all less than the energy threshold, the formula is according to a relation between LOR and FOV to picks out the data corresponding to coincident event from the data corresponding to triple event.

13. A method for reusing triple event data of positron emission tomography, comprising:
obtaining a plurality of data is generated by a positron emission tomography scan device, wherein the data comprising different events with photons detected;
dropping out the data corresponding to single event;
picking out the data corresponding to double event;
picking out the data corresponding to triple event from the data, and calculating three parameters of time difference of three photons arriving a detector, three lengths of line of response (LOR) and total activity of the three LOR through the object in triple event to obtain three first probability values by a formula;
determining whether one of the largest first probability value is greater than twice of the sum of the other two first probability values, if yes, picking out the data with the largest first probability value, if not, dropping out the data; and
analyzing the data which have not been dropped out to generate an analysis result.

14. The method according to claim 13, wherein the each first probability value is the product of the time probability of a photon arriving the detector, the length probability of LOR and total activity probability of the LOR through the object.

15. The method according to claim 13, further comprising:
calculating the first probability values, the situation if the photon through the object and the photon energy in triple event, to obtain three second probability values; and
determining whether one of the largest second probability value is greater than twice of the sum of the other two second probability values, if yes, picking out the data with the largest second probability value, if not, dropping out the data.

16. The method according to claim 15, wherein the each second probability value is the product of the first probability value, the probability of the photon through the object and photon energy probability.

17. The method according to claim 13, wherein a positron emitter of the positron emission tomography is non-pure positron emitter or pure positron emitter.

18. The method according to claim 17, wherein the non-pure positron emitter comprises $^{22}$Na、$^{124}$I、$^{76}$Br、$^{86}$Y.

19. The method according to claim 17, wherein the pure positron emitter comprises $^{11}$C、$^{13}$N、$^{15}$O、$^{18}$F.

20. The method according to claim 13, wherein the formula is according to a relation between LOR and field of view (FOV) to picks out the data corresponding to coincident event from the data corresponding to triple event.

21. The method according to claim 20, wherein the formula is according to a relation between LOR, FOV and photon energy to picks out the data corresponding to coincident event from the data corresponding to triple event.

22. The method according to claim 13, wherein the formula is according to a relation between the energy of the three photons and an energy threshold to picks out the data corresponding to coincident event from the data corresponding to triple event.

23. The method according to claim 22, when the energy of the one of the three photons detected is larger than the energy threshold, and the energy of the other two photons are both less than the energy threshold, the other two photons are determined to a pair of annihilation photons.

24. The method according to claim 23, when the energy of the three photons detected are all less than the energy threshold, the formula is according to a relation between LOR and FOV to picks out the data corresponding to coincident event from the data corresponding to triple event.

* * * * *